United States Patent [19]
Ross et al.

[11] Patent Number: 5,789,187
[45] Date of Patent: Aug. 4, 1998

[54] IDENTIFICATION OF DIFFERENTIATION FACTOR RECEPTORS WHICH INHIBIT THE TUMORIGENICITY OF NEUROBLASTOMA CELLS IN A LIGAND-INDEPENDENT MANNER

[75] Inventors: Alonzo H. Ross; Wojciech Poluha; Mahesh B. Lachyankar; Dorota K. Poluha, all of Shrewsbury, Mass.

[73] Assignee: Worcester Foundation for Experimental Biology, Shrewsbury, Mass.

[21] Appl. No.: 310,287

[22] Filed: Sep. 21, 1994

Related U.S. Application Data

[63] Continuation-in-part of Ser. No. 936,923, Aug. 27, 1992, Pat. No. 5,387,520.

[51] Int. Cl.$^6$ .................... C12Q 1/02; A61K 31/70; C12N 15/12
[52] U.S. Cl. .................... 435/29; 514/44; 435/240.2; 435/240.25; 435/69.1; 935/62
[58] Field of Search .................... 514/44; 435/69.1, 435/29, 34, 240.25, 240.2; 935/62

[56] References Cited

U.S. PATENT DOCUMENTS 5,387,520 2/1995 Lopresti et al. .................... 435/240.2

FOREIGN PATENT DOCUMENTS

WO 94/05315 3/1994 WIPO.
WO 94/17407 8/1994 WIPO.

OTHER PUBLICATIONS

Colombo et al. (1991) *J. Exp. Med.* 173:889–897.
Pleasure et al. (1990) *Proc. Natl. Acad. Sci. USA* 87:8496–8500.
Missale et al. (1993) *Proc. Natl. Acad. Sci. USA* 90:7961–7965.
Colamonici, O. R., et al. (1994) *J. Biol. Chem.* 269(44): 27275–79.
Obermeier, A., et al. (1993) *EMBO J* 12:933–41.
Rovelli, G., et al. (1993) *Proc. Natl. Acad. Sci. USA* 90: 8717–21.
Hempstead, B.L., et al. )1992) *Neuron* 9: 883–96.
Traverse et al. (1994) *Current Biol.* 4:694–708.
Nishikawa et al. (1994) *Proc. Natl. Acad. Sci. (USA)* 91:7727–7731.
Wu et al. (1994) *J. Neurosci.* 14:4806–4814.
Nakagawara et al. (1994) *Mol. Cell. Biol.* 14:(1):759–767.
Ross et al. (1994) *Proc. Amer. Assoc. Cancer Res.: Clinical investigations* 35:252 (Abstract 1504).
Kogner et al. (1993) *Cancer Res.* 53:2044–2050.
Nakagawara et al. (1993) *New Engl. J. Med.* 328:847–854.
Suzuki et al. (1993) *J. Natl. Cancer Inst.* 85:377–384.
Ip et al. (1993) *Neuron* 10:137–149.
Matsushima et al. (1993) *Mol. Cell. Bio.* 13:7447–7456.
Flotte et al. (1993) *Proc. Natl. Acad. Sci. (USA)* 90:10613–10617.
Kaplan et al. (1993) *Neuron* 11:321–331.
Zabner et al. (1993) *Cell* 75:207–216.
Richter et al. (1993) *Cancer Res.* 53:4134–4137.
Fujiwara et al. (1993) *Cancer Res.* 53:4129–4133.
Ciardiello et al. (1993) *Int. J. Cancer* 54:952–958.
Hao et al. (1993) *Nature* 365:764–767.
Matsushima et al. (1993) *Advances in Neuroblastoma Research No. 6* (The Children's Hospital of Philadelphia).
LoPresti et al. (1992) *Cell Growth Diff.* 3:627–635.
Jensen et al. (1992) *J. Biol. Chem.* 267:19325–19333.
Ibanez et al. (1992) *Cell* 69:329–341.
Cattaneo et al. (1991) *TINS* 14:338–340.
Kaplan et al. (1991) *Science* 252:554–558.
Klein et al. (1991) *Cell* 65:189–197.
Squinto et al. (1991) *Cell* 65:885–893.
DiCicco–Bloom et al. (1990) *J. Cell. Bio.* 110:2073–2086.
Chen et al. (1990) *Cell Growth Diff.* 1:79–85.
Matsushima et al. (1990) *Mol. Cell. Biol.* 10:(9):5015–5020.
D'angio et al. (1990) *The Fifth Symposium On Neuroblastoma Research* (The Children's Hospital of Philadelphia).
Rudkin et al. (1989) *EMBO J.* 8:3319–3325.
Hempstead et al. (1989) *Science* 243:373–375.
McConnell (1988) *J. Neurosci.* 8:945–974.
Turner et al. (1987) *Nature* 328:131–136.
Rohrer et al. (1987) *J. Neurosci.* 7:3739–3748.
Jensen (1987) *Dev. Biol.* 120:56–64.
Greenberg et al. (1985) *J. Biol. Chem.* 260:14101–14110.
Purves et al. (1985) *Principles of Neural Development*, Sinauer Assoc. Inc. Publishers, Sunderland, MA, p. 27.
Sonnenfeld et al. (1985) *J. Neurosci.* 5:1717–1728.
Evans et al. (1980) *Cancer* 45:833–839.
Knudson et al. (1980) *New Engl. J. Med.* 302:1254–1256.
Greene et al. (1976) *Proc. Natl. Acad. Sci. (USA)* 73:2424–2328.
Lee et al. *Strategies in Mol. Biol.* 7:28–31.
Tannock et al., *The Basic Science of Oncology* 2nd ed., CH. 9, pp. 139–143.

*Primary Examiner*—David L. Fitzgerald
*Attorney, Agent, or Firm*—Lappin & Kusmer LLP

[57] ABSTRACT

Disclosed is a method of reducing or inhibiting the tumorigenicity of a tumor cell in which a vector including a nucleotide sequence encoding a differentiation factor receptor, or a polypeptide portion thereof, is transferred to the tumor cell such that the nucleotide sequence is expressed. Tumorigenicity is monitored by cell growth and colony formation in a semi-soft medium, a reduction in proliferation being indicative of the reduction or inhibition of tumorigenicity of the treated tumor cell.

11 Claims, 10 Drawing Sheets

IDENTIFICATION OF DIFFERENTIATION FACTOR RECEPTORS WHICH INHIBIT THE TUMORIGENICITY OF NEUROBLASTOMA CELLS IN A LIGAND-INDEPENDENT MANNER

CROSS-REFERENCE TO RELATED APPLICATIONS

This application is a continuation-in-part of patent application Ser. No. 07/936,923 entitled "TREATMENT OF TUMORS WITH NEUROTROPHIC FACTORS AND CELL PROLIFERATION INHIBITORS," filed Aug. 27, 1992 now U.S. Pat. No. 5,387520.

FUNDING

This invention was made with Government support under NIH grant no. R01 NS21716 awarded by the National Institutes of Health. Accordingly, the U.S. Government has certain rights in this invention.

BACKGROUND OF THE INVENTION

The technical field of this invention is gene therapy. More particularly, this invention relates to the treatment of cancer cells and the inhibition of their tumorigenicity by the transfer into and expression of a gene encoding a receptor for a differentiation-inducing factor in cancer cells.

The nervous system is derived from multipotential precursor cells that maintain a closely regulated inverse relationship between cell proliferation and differentiation (Cattaneo et al. (1991) TINS 14:338–340). In the central nervous system, these precursor cells commit to a specific differentiation pathway shortly after the last mitosis (McConnell (1988) J. Neurosci. 8:945–974; Turner et al. (1987) Nature 328:131–136). In the peripheral nervous system, sensory neurons differentiate following withdrawal from the cell cycle (Rohrer and Thoenen (1987) J. Neurosci. 7:3739–3748), but sympathetic neuroblasts begin to differentiate while still mitotically active (DiCicco-Bloom et al. (1990) J. Cell. Bio. 110:2073–2086). The molecular basis of the coupling between neuronal differentiation and cell proliferation is a problem of current interest.

The coupling between neuronal differentiation and cell proliferation also is relevant to the etiology of neural tumors, such as neuroblastoma in which the regulation of these two cell processes is disrupted. Neuroblastoma is one of the most common pediatric solid tumors, frequently occurring in infancy with the primary lesion in the adrenals and sympathetic chain (Voute, "Neuroblastoma" in Clinical Pediatric Oncology (Sutow et al., eds.) (1984) pp. 559–587). This tumor is difficult to treat as common modes of chemotherapy have harsh side effects on normal infant tissue. Interestingly, neuroblastomas are noted for their ability to undergo spontaneous regression or maturation to benign ganglioneuromas (Evans et al. (1980) Cancer 45:833–839). The similarity of neuroblastoma cells to neuroblasts and their ability to spontaneously mature to a more benign form suggest that the disease may originate by a block of differentiation of a sympathetic precursor cell (Knudson et al. (1980) New Engl. J. Med. 302:1254–1256). Hence, factors which promote the differentiation of proliferating neuroblastic cells are candidates for new therapeutic approaches. Due to the side effects of cancer therapy, there is great need for "natural" but highly-specific pharmaceutical treatments.

Recent clinical studies suggest that TrkA, a nerve growth factor (NGF) receptor with a tyrosine kinase domain (Kaplan et al. (1991) Science 252:554–558; Klein et al. (1991) Cell 65:189–197) plays a critical role in this disease. Patients whose tumors express significant levels of TrkA have a good chance for survival, while patients whose tumors lack TrkA respond poorly to therapy (Kogner et al. (1993) Cancer Res. 53:2044–2050; Nakagawara et al. (1993) New Engl. J. Med. 328:847–854; Suzuki et al. (1993) J. Natl. Cancer Inst. 85:377–384). Thus, the expression of TrkA appears to be dependent on a later stage of differentiation of the neuroblastoma cells. Accordingly, if the cancer cell expresses the receptor, it can be receptive to and hence influenced by treatment with the differentiation factor specific for the receptor, thereby causing it to be less tumorigenic than a tumor cell that does not express the receptor.

Thus, what is needed are methods of treating tumor cells such that their ability to differentiate is enhanced, thereby reducing their tumorigenicity. Also needed are methods of reducing tumorigenicity of tumor cells.

SUMMARY OF THE INVENTION

It has been discovered that if a gene encoding a receptor for a differentiation factor is incorporated into a cancer cell, the tumorigenicity of the cell is reduced, while its morphology remains basically unaffected. Surprisingly, this reduction in tumorigenicity does not require the presence of the differentiation factor for which the receptor is specific. These findings have been exploited to develop the present invention which includes methods of treating a tumor cell in vitro, and of inhibiting or reducing its tumorigenicity.

As used herein, the term "tumorigenicity" is meant to encompass the ability of a cell to form a tumor as measured by the ability of the cell to form a colony in semi-solid medium.

In the methods of the invention, a vector is provided which contains a nucleotide sequence encoding a receptor, or a polypeptide portion thereof, for a differentiation factor. As used herein, the term "vector" is meant to encompass a structure composed of covalently linked nucleotides which is able to enter a cell with the receptor-encoding nucleotide sequence.

A "receptor" encompasses molecules on the surface of a cell membrane or partially within the cell membrane and partially exposed on the external surface to which a differentiation factor bind. These receptors may be homologous, i.e., having all of their domains encoded by genes for a single type of receptor. Alternatively, the receptor may be chimeric, i.e., having at least a portion or domain which is encoded by genes for different receptors that have been fused together such that, e.g., the extracellular domain is derived from one receptor and the intracellular or transmembranes domain is derived from a second receptor.

In preferred embodiments, the vector is an expression vector, plasmid, retrovirus, adenovirus, adeno-associated virus, Herpesvirus, or episomal vector.

The term "differentiation factor" as used herein refers to any molecule or complex of molecules which causes a cell to evolve from one state to another which may have a decreased proliferative capacity and/or diminished capacity to choose other differentiated pathways, i.e., the cell becomes more committed to one pathway and less able to redirect itself to another. A differentiated cell may have an altered morphology associated with one lineage or differentiated state, and may express genes associated with one particular lineage or differentiated state. For example one type of differentiation factor (called a neurotrophin) may cause small, round neuroblastoma cells to become extended and develop neurite outgrowths.

In some embodiments, the differentiation factor for which the receptor is specific, is nerve growth factor (NGF), an interleukin, fibroblast growth factor, neurotrophin-3, neurotrophin-4, insulin-like growth factor, retinoic acid, or brain derived neurotrophic factor. In other embodiments, the receptor gene encodes at least a polypeptide portion or domain of TrkA (which is the receptor for NGF), TrkB (which is the receptor for brain derived neurotrophic factor), TrkC (which is the receptor for neurotrophin-3), an epidermal growth factor receptor, a fibroblast growth factor receptor, an insulin-like growth factor, a retinoic acid receptor, a platelet receptor growth factor receptor, a brain derived neurotrophic factor receptor, or an interleukin receptor.

The vector containing the differentiation factor receptor nucleotide sequence is transferred to the tumor cell such that the sequence is expressed in the cell. In preferred embodiments, transference is accomplished by electroporation, transfection, transformation or injection with a viral vector, or by particle bombardment.

As used herein, "electroporation" refers to the transfer of a nucleotide sequence by formation of hydrophilic pores in a cell membrane by the electric field. "Transfection" refers to the transfer of a nucleotide sequence via physical uptake of the nucleic acid, e.g., either as a calcium phosphate precipitate or complexed with DEAE dextran. "Particle bombardment" refers to a method wherein small particles are coated with DNA and then propelled at high speed into the cell.

In some embodiments, the nucleotide sequence is incorporated into the genome of the cell. In other embodiments, the nucleotide sequence remains separate from the cell genome with the vector which is an independent episome or attached to the particle following particle bombardment.

If the transfer is successful, a reduction in cell proliferation in semi-solid medium, and hence a reduction in tumorigenicity, is detected as compared with the level or rate of cell proliferation present before the transfer.

As used herein, "semi-solid medium" refers to a medium which is not liquid or solid, such as soft agar, soft agarose, or soft methylcellulose.

In one embodiment, the detecting step includes culturing the cells containing the vector in vitro, counting the number and size of the resulting colonies, and comparing the number and size of the colonies formed from cells which had not been treated with the vector, a reduction in the number and size of the colonies being indicative of a reduction in tumorigenicity. In preferred embodiments, the cells containing the transferred nucleotide sequence are cultured in soft agarose or methylcellulose.

The tumor cells which are affected by the method of the invention are any type of cancerous cell such as those grown in culture or as explants of in vivo tumors. In some embodiments, such cells include neuroblastoma, lymphoma, carcinoma, leukemic, astrocytomas, and glioblastoma cells.

The present invention also provides a method of screening for receptor molecules which inhibit the tumorigenicity of neuroblastoma cells. In this method, a plurality of vectors is provided which each contain a nucleotide sequence encoding a differentiation factor receptor, or a polypeptide portion thereof. The vectors are transferred to a culture of neuroblastoma cells such that the nucleotide sequence encoding the receptor is expressed in the cells. The cell culture is then monitored for colony formation and colony size in semi-solid medium, a reduction in formation and in colony size being indicative of the presence of a receptor which has an inhibitory effect on neuroblastoma cell tumorigenicity.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patents, allowed applications, and other publications cited herein are hereby incorporated by reference.

This invention provides a method of treating tumor cells which results in a reduction in their ability to proliferate in semi-soft media and hence in their tumorigenicity. In this method, a gene encoding a differentiation factor receptor or portions thereof, or nucleotide sequences encoding portions of different differentiation factor receptor are transferred to the tumor cells. The expression of this gene(s) in the tumor cell results in an inhibition of tumorigenicity as measured by a decrease in, or reduced, proliferation in semi-soft media such as soft agarose.

The cells that can be treated by this method include any tumor cell such as neuroblastoma, carcinoma, lymphoma, glioblastoma, astrocytoma, and the like, which allow the entry and expression of the transferred nucleotide sequence therein. These cells may be in vivo, an in vitro culture, or an in vitro cultured explant of a tumor.

The differentiation factors which the receptor recognizes includes any peptide-containing molecule which has the effect of causing a morphological and physiological change in a cell when bound and sometimes internalized. Useful differentiation factor include but are not limited to, nerve growth factor (NGF), interleukins, fibroblast growth factor (FGF), epidermal growth factor (EGF), neurotrophins, insulin-like growth factor (IGF), retinoic acid, platelet derived growth factor (PDGF), and brain derived neurotrophic factor (BDGF).

Figure 15:
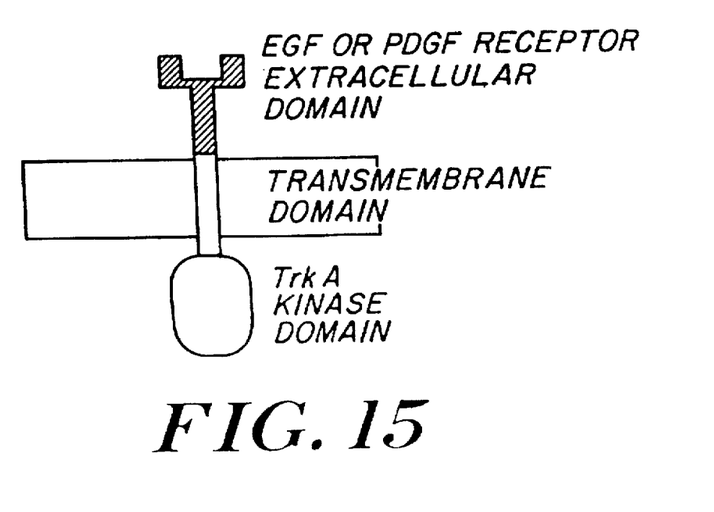
FIG. 15 is a schematic representation of a chimeric receptor resulting from pLXSN-ET-R in which the extracellular and transmembranous domains are derived from the EGF or PDGF receptor and the intracellular domain is derived from TrkA.

Useful receptors encoded by the gene to be transferred include, but are not limited to, TrkA, TrkB, TrkC, fibroblast growth factor receptor, insulin-like growth factor, retinoic acid receptor, interleukin receptors, and the like whose nucleotide sequences are known. The transferred nucleotide sequence alternatively may encode only part of a receptor, such as an external, transmembranous, or internal domains or may encode chimeric receptors having domain, from different receptors. Such chimeric receptor genes may be prepared by fusing together nucleotide sequences known to encode desired receptor domains. Useful fusions include EGF receptor or PDGR receptor extracellular domains, and the TrkA intracellular domain (see FIG. 15).

The nucleotide sequence encoding the receptor, or portion thereof, is transferred to the tumor cell via a vector capable of entering the cell through various techniques. This vector may be an expression vector, retrovirus, adenovirus, Herpesvirus, or other transfer vehicle known in the art which integrates into the cell genome once inside. Alternatively, the nucleotide sequence may be a part of an episome or attached to a particle (used in particle bombardment) which remains separate from the cell genome and is capable of independent replication and expression. Preparation of such vectors and the integration of the nucleotide sequence encoding the receptor are well known in the art (see, e.g., Sambrook et al. (1989) *Molecular Cloning, A Laboratory Manual*, Cold Spring Harbor Laboratory Press, pp. 3.2–3.58; Krieger (1990) *Gene Transfer and Expression*, Stockton Press, Wyo.; Wolff (ed.) *Gene Therapeutics*, Birkhauser Press, Boston, Mass., 1994).

Transference of the nucleotide sequence can be accomplished via any known method, such as transfection. For example, calcium phosphate- or DEAE-dextran-mediated transfection enables a nucleotide sequence to enter a cell by endocytosis. The nucleic acid sequence is then transferred to the nucleus where it can be expressed by the protein synthetic machinery of the cell (see, e.g., Sambrook et al., *ibid.*, pp. 16.33–16.46). In addition, the polycation polybrene allows the introduction of low molecular weight DNAs into cell lines that are relatively resistant to transfection by other methods (see, e.g., Sambrook et al., *ibid.*, p. 16.47).

Another mode of transferring a nucleotide sequence into a cell is protoplast fusion. In this method, protoplasts derived from bacteria carrying high numbers of copies of a plasmid of interest are mixed directly with cultured mammalian cells. After fusion of the cell membranes, usually with polyethylene glycol, the contents of the bacteria are delivered into the cytoplasm of the cells and the plasmid is transferred to the nucleus (see, e.g., Sambrook et al., *ibid.*, p. 16.48–53).

Yet another method of delivering the nucleotide sequence to a cell is electroporation, which involves the application of brief, highvoltage electric pulses to the cells, leading to the formation of nanometer-sized pores in the plasma membranes. DNA is taken directly into the cell cytoplasm either through these pores or as a consequence of redistribution of membrane components that accompanies closure of the pores (see, e.g., Sambrook et al., *ibid.*, pp. 16.54–55).

The tumor cells are then examined to determine if their tumorigenic abilities have been diminished by the above treatment. If the cells are in the form of an in vivo tumor, its size can be monitored by physical measurement, NMR, or other non-invasive scanning techniques. Alternatively, a tumor explant can be obtained and its growth in soft agarose monitored. Yet another method of measuring tumorigenicity is culturing individual tumor cells in soft agarose and monitoring proliferation and colony size.

The invention also provides a therapeutic composition including the vector described above and a physiologically acceptable carrier.

As used herein, a "physiologically acceptable carrier" includes any and all solvents, dispersion media, coatings, antibacterial and antifungal agents, isotonic and absorption delaying agents and the like which will not inactivate the ability of the vector to express itself in the neuroblastoma cell or to integrate into its genome of the cell. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The differentiation factor receptor-encoding vectors of the invention may also be used to treat neuroblastoma cells in humans and other mammals. In this method, the vector including the gene encoding the receptor for a differentiation factor is administered once in the form of a pharmaceutical composition in a therapeutically effective amount, or repeatedly in less than therapeutic amounts. Administration may be by direct injection into the tumor. Effective dosages of the vector and modes of its administration in the treatment of neuroblastoma can be determined by routine experimentation. The pharmaceutical forms suitable for injection or other use include sterile aqueous solutions or dispersions. In all cases the form must be sterile. It must be stable under the conditions of manufacture and storage and may be preserved against the contaminating action of microorganisms, such as bacteria and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

It is known that the differentiation factor, NGF, acts synergistically with aphidicolin, a highly specific and reversible inhibitor of DNA polymerases α and δ, to induce terminal differentiation of neuroblastoma cells such as SHSY5Y (LoPresti et al. (1992) *Cell Growth Diff.* 3:627–635; Jensen (1987) *Dev. Biol.* 120:56–64). Treatment with the differentiation factor, alone, does not stop cell proliferation and induces only slight neurite extension (Chen et al., (1990) *Cell Growth Diff* 1:79–85). Treatment with aphidicolin, alone does not induce neurite extension. However, treatment with aphidicolin, alone stops cell proliferation, but proliferation resumes when the drug is removed. In contrast, cells treated simultaneously with a cell differentiation factor (such as NGF) and a pulse of a cell proliferation inhibitor (such as aphidicolin) cease cell proliferation and extend long neurites (see copending patent application Ser. No. 07/936,923now U.S. Pat. No. 5,387, 520). The differentiated cells require the cell differentiation factor for survival, but if maintained in the presence of the factor, the neuroblastoma cells with long neurites are stable for at least 4 to 6 weeks. These cells express many neuronal markers and resemble sympathetic neurons. Despite the dramatic change in morphology, expression of a relatively small number of polypeptides is altered following differentiation (Jensen et al. (1992) *J. Biol. Chem.* 267:19325–19333).

Other treatments which block cell proliferation also enhance NGF-induced differentiation. Both hydroxyurea and thymidine, which inhibit synthesis of nucleotides, act synergistically with NGF to induce differentiation of SYSH5Y cells (LoPresti et al. (1992) *Cell Growth Diff.* 3:627–635; Jensen (1987) *Dev. Biol.* 120:56–64). In addition, NGF-induced differentiation of PC12 cells is enhanced by serum-deprivation (Rudkin et al. (1989) *EMBOJ.* 8:3319–3325).

It has been shown that cell growth and transformation of NIH-3T3 cells expressing trkA, trkB, and trkC occurs upon continuous stimulation of the receptor cascade with a preferred neurotrophic ligand (Ip et al. (1993) *Neuron* 10:137–149). In addition, nude mouse tumors expressing the trkA gene have been shown to differentiate into nontumorogenic neural components upon treatment with NGF (Matsushima et al. (1993) *Mol. Cell. Biol.* 13:7447–7456).

Figure 1:
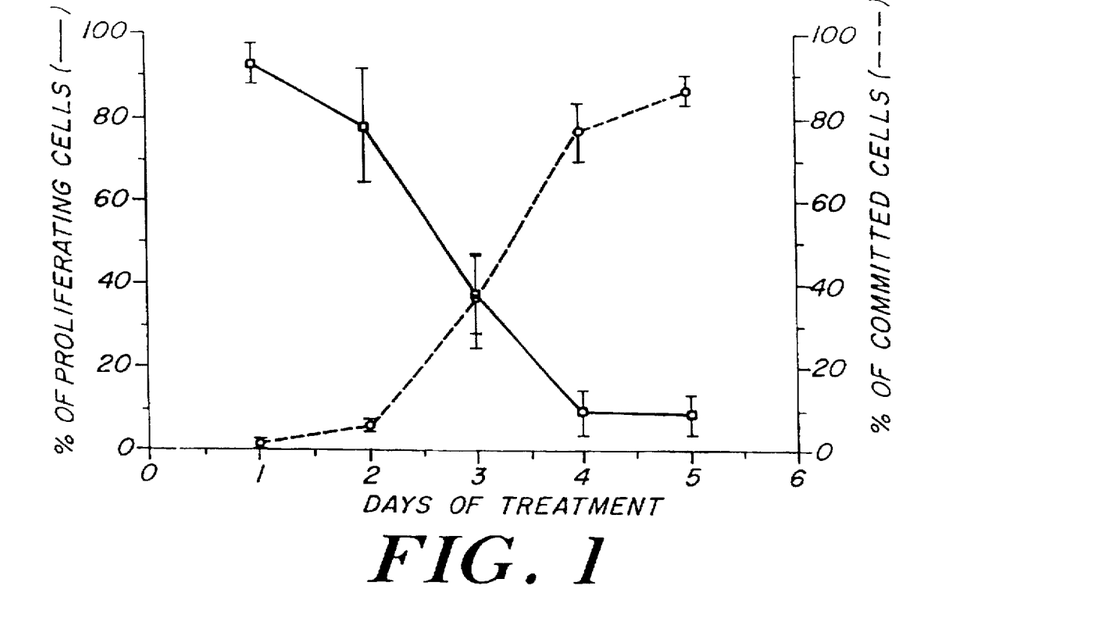
FIG. 1 is a graphic representation of the relation between commitment to differentiation and irreversible cessation of proliferation.

To assess the length of time required for commitment to differentiation, cells were treated for 1–5 days with NGF and aphidicolin, 6 days with NGF, and then scored for neurite extension (FIG. 1). In this assay, cells which extended neurites are taken as those which had committed to differentiation at the end of the NGF and aphidicolin treatment. Significant extension of neurites required treatment of the neuroblastoma cells with NGF and aphidicolin for 3 to 4 days, and differentiation was maximal (75–90% of cells) after 5 days of treatment. For all of these cultures, there was little cell death (i.e., viability was greater than 90%). As judged by bromodeoxyuridine (BrdU) labelling, SHSY5Y cells treated with NGF and aphidicolin and then with NGF showed greatly reduced cell proliferation (FIG. 1). Commitment to differentiation and irreversible cessation of cell proliferation appeared to occur simultaneously after 3 to 4 days of treatment with NGF and aphidicolin.

Figure 2:
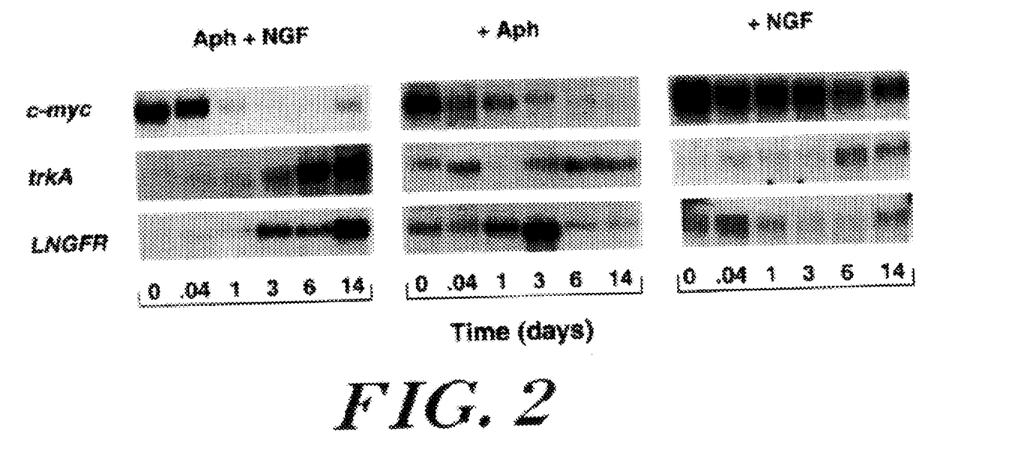
FIG. 2 is a Northern blot of poly $A^+$ RNA from SHSY5Y cells treated for varied periods of time with NGF and aphidicolin (Aph); Aph alone; or NGF alone, and then probed with c-myc, trkA, and the low affinity NGF receptor (LNGFR) genes. For the 14 day samples, Aph- and NGF-treated cells were fully differentiated by treatment with NGF and Aph for 6 days and with NGF for 8 days; Aph-treated cells were treated with Aph for 6 days and with normal growth medium for 8 days; and NGF-treated cells were treated with NGF for 14 days.

Expression of a number of genes relevant to cell proliferation and differentiation was assessed by Northern blotting (FIG. 2). Expression of c-myc was downregulated following treatment for 1 day with aphidicolin or with NGF and aphidicolin. Treatment with NGF induced only a slight downregulation of c-myc. Expression of trkA NGF receptor was upregulated following treatment for 3 to 4 days with NGF and aphidicolin. Treatment with aphidicolin alone had no significant effect on trkA expression, but long treatments with NGF induced a slight upregulation of trkA. Expression of the low affinity NGF receptor also was synergistically upregulated by treatment for 3 to 4 days with NGF and aphidicolin. Ethidium bromide staining of RNA prior to transfer, as well as rehybridization of filters with the δ-actin probe, confirmed that the RNA was intact and the difference in mRNA levels could not be attributed to unequal loading. Hence, a succession of molecular events leading to differentiation was established. Downregulation of c-myc was an early event, whereas upregulation of trkA and the low affinity NGF receptor occurred about the time of commitment to differentiation.

Expression of two other mRNAs also was assessed by Northern blotting. The protein encoded by c-myc is thought to act in a complex with the protein encoded by c-max (Blackwood et al. (1991) *Science* 251:1211–1217. Unlike c-myc, the expression of c-max was not altered during differentiation of SHSY5Y cells. Also, the mRNA for trkB, another member of the trk family of neurotrophic receptors (Squinto et al. (1991) *Cell* 65:885–893), was not detected in any of these samples.

To test the role of the low affinity NGF receptor in neuroblastic differentiation, anti-low affinity NGF receptor monoclonal antibody ME20.4 (Ross et al. (1984) *Proc. Natl. Sci. USA* 81:6681–6685) was added to SHSY5Y tumor cells in addition to NGF and aphidicolin. There was no apparent decrease in the rate or extent of differentiation. Since ME20.4 antibody blocks binding of NGF to the low affinity NGF receptor, these results suggest that the receptor, itself is not required for differentiation of these cells.

Figure 3A:
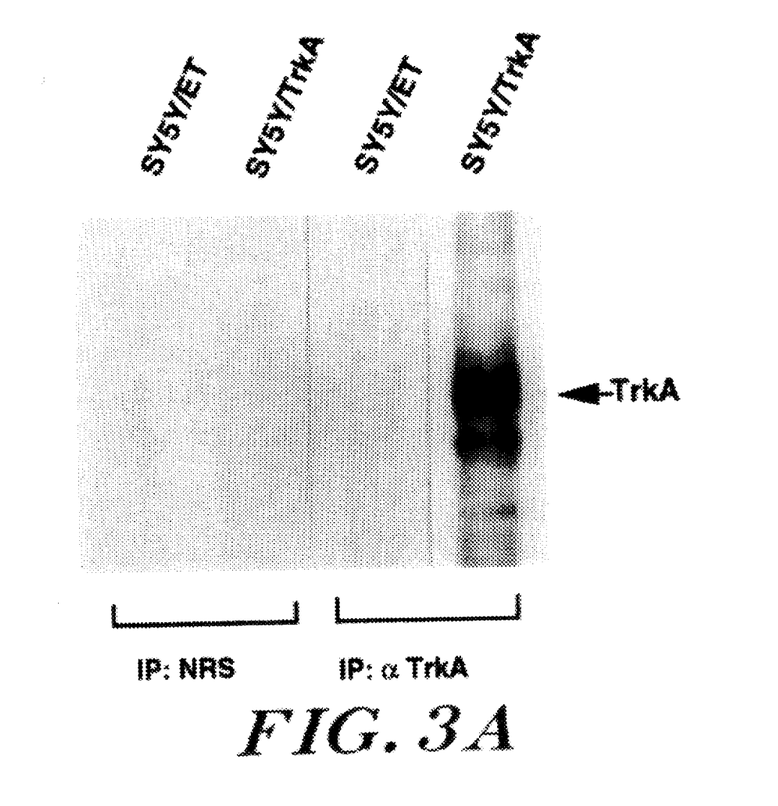
FIG. 3A is an autoradiogram showing the metabolic labelling and immunoprecipitation of TrkA from SY5Y/ET and SY5T/TrkA cells labelled with [$^{35}$S] methionine, and membrane extracts immunoprecipitated with normal rabbit serum (NRS) or anti-TrkA antiserum ($\alpha$TrkA)
Figure 3B:
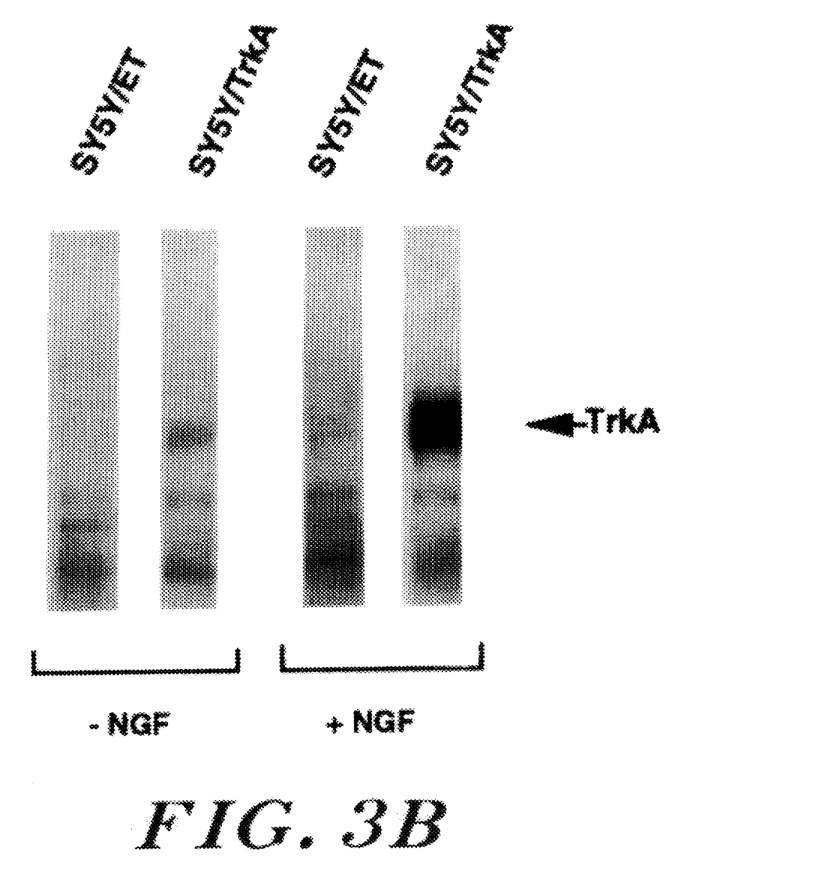
FIG. 3B is a Western blot showing the immunoprecipitation of TrkA from SY5Y/ET and SY5T/TrkA cells treated with 0 or 100 ng/ml NGF for 10 min., extracted, and immunoprecipitated with anti-TrkA antibody. Phosphorylation of tyrosine residues was detected with an anti-phosphotyrosine antibody-peroxidase conjugate.

To determine the role of the TrkA receptor in neuroblastic differentiation, the TrkA expression vector pIRVCMV-TrkA, or the corresponding vector lacking the trkA insert, were introduced into SHSY5Y or LAN5 cells by electroporation. Selection was carried out with 400 μg/ml of G418, resulting in the TrkA-expressing cell lines SY5Y/TrkA LAN5/TrkA and the control lines SY5Y/ET LAN5/ET. A 140,000 dalton TrkA product was immunoprecipitated from SY5Y/TrkA cells, but there was no apparent TrkA product in SY5Y/ET cells, as shown in the autoradioagram in FIG. 3A. NGF treatment of SY5Y/TrkA cells, but not SY5Y/ET cells, resulted in phosphorylation of TrkA on tyrosine residues (FIG. 3B). These results suggest that TrkA is required for a cellular response to NGF, and that SY5Y/ET cells have little if any endogenous TrkA.

Figure 4A:
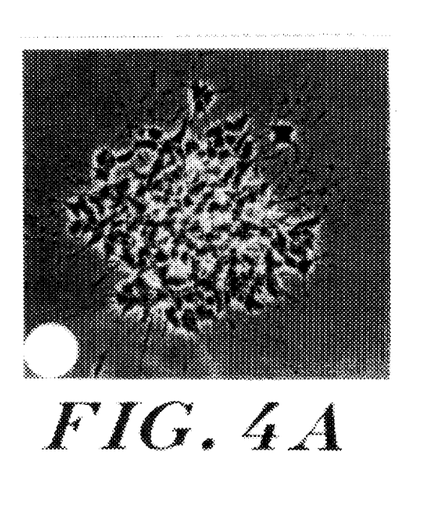
FIG. 4A is a phase contrast micrograph of SY5Y/ET cells cultured for 2 weeks without NGF.
Figure 4B:
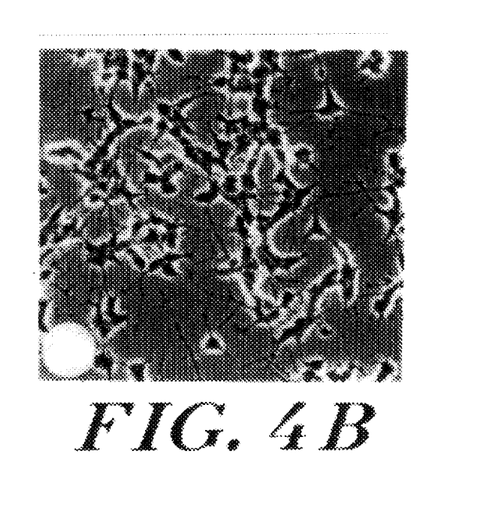
FIG. 4B is a phase contrast of SY5Y/ET cells cultured for 2 weeks with 100 ng/ml NGF.
Figure 4C:
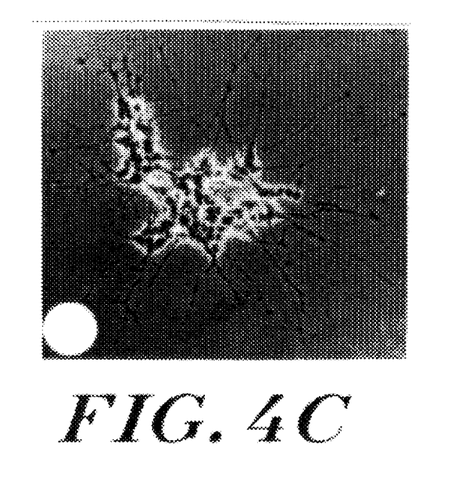
FIG. 4C is a phase contrast micrograph of SY5Y/TrkA cells cultured for 2 weeks without NGF.

For both SY5Y/ET and SY5Y/TrkA, the cell morphology differed slightly from the parent line. Roughly 50% of the cells were present in cell aggregates (FIGS. 4A and 4B), which were only rarely seen for the parent line. SY5Y/TrkA cells displayed slightly longer neurites than SY5Y/ET cells, indicating that the trkA-containing cells were more differentiated.

Figure 4D:
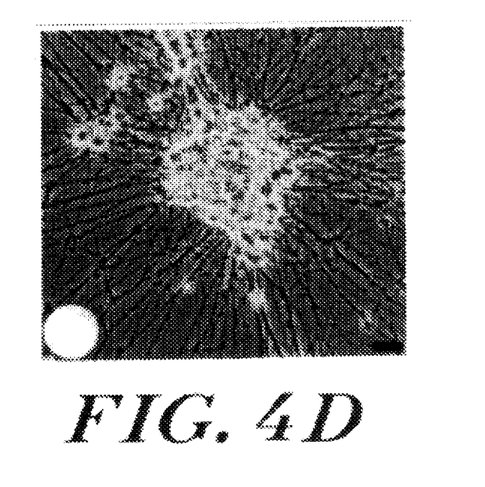
FIG. 4D is a phase contrast micrograph of SY5Y/TrkA cells cultured for 2 weeks with 100 ng/ml NGF (bar=25 µm)
Figure 5:
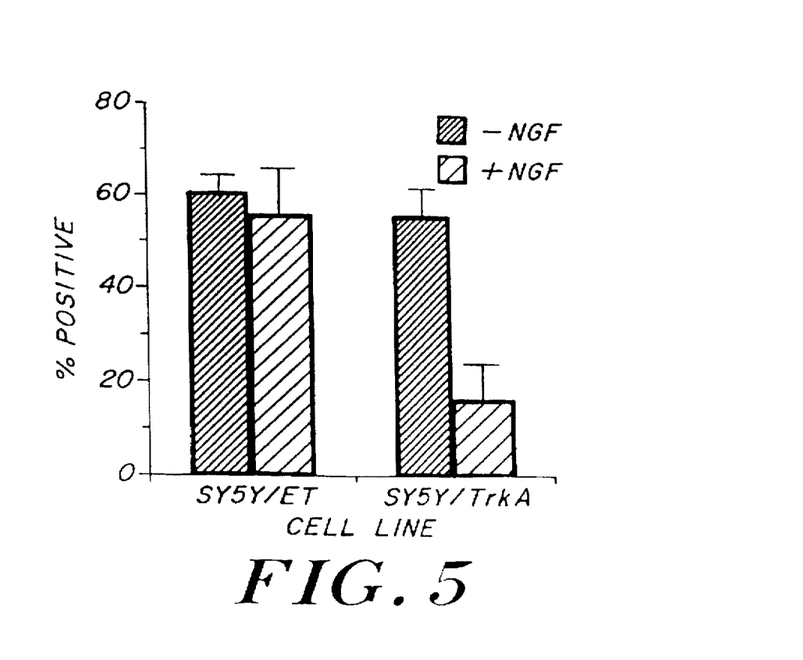
FIG. 5 is a bar graph showing the percentage of SY5Y/ET or SY5Y/TrkA cells (±S.D.) positive for BrdU staining after treatment for 2 weeks without or with 100 ng/ml of NGF.
Figure 6A:
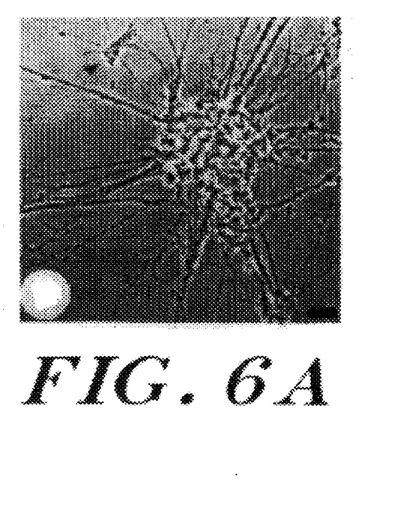
FIG. 6A is a phase-contrast micrograph of aggregated, differentiated SY5Y/TrkA cells and two undifferentiated SY5Y/TrkA cells (arrowhead)
Figure 6B:
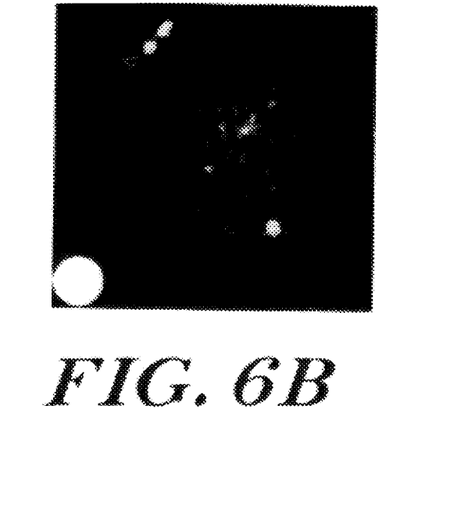
FIG. 6B is a fluorescent micrograph of SY5Y/TrkA cells labeled with BrdU and a fluorescent anti-BrdU antibody (arrowhead shows strongly labelled undifferentiated cells)
Figure 7:
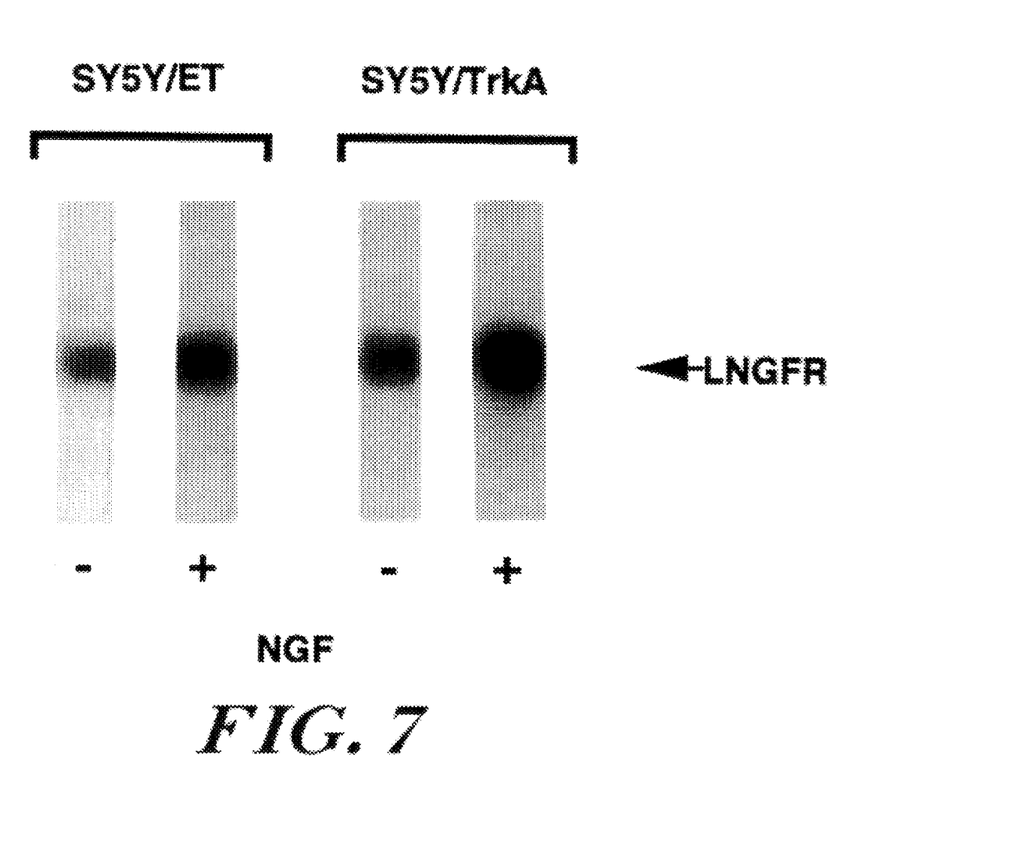
FIG. 7 is a Northern blot of poly A+RNA from SYSY/ET or SY5Y/TrkA cells treated with 0 or 100 ng/ml NGF and probed for the low affinity NGF receptor (LNGFR)

The responses of SY5Y/ET and SY5Y/TrkA to NGF were assessed. Treatment of SY5Y/ET cells with NGF resulted in a slight extension of neurites (FIG. 4B), but there was no effect of NGF on cell proliferation as judged by BrdU labelling (FIG. 5). In contrast, SY5Y/TrkA cells treated with NGF extended long neurites and formed aggregates of cell bodies (FIG. 4D). Treatment of SY5Y/TrkA cells with NGF greatly reduced labelling with BrdU (FIG. 5). In particular, there was virtually no labelling of the SY5Y/TrkA cells with a strongly differentiated morphology (FIG. 6A and 6B). Those cells which did label (FIG. 6A and 6B arrowheads) resembled the parental line. Furthermore, treatment of SY5Y/TrkA and SYSY/ET cells with NGF enhanced expression of the mRNA for the low affinity NGF receptor, but the level of the mRNA for the low affinity NGF receptor (LNGFR) was about 3-fold greater for SY5Y/TrkA cells than for SY5Y/ET cells (FIG. 7). Hence, expression of TrkA greatly enhanced the capability of SHSY5Y cells to differentiate and to express the low affinity NGF receptor.

Figure 8A:
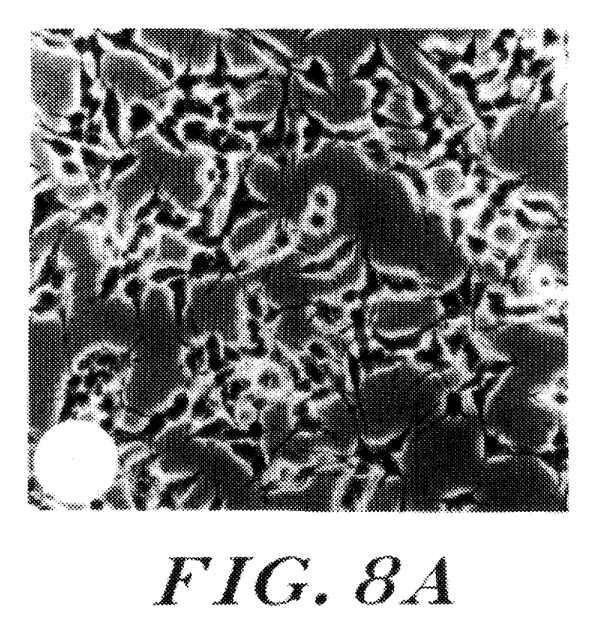
FIG. 8A is a phase contrast micrograph of SY5Y/ET cells treated for 8 days with 100 ng/ml NGF and then with normal growth medium for 6 days (bar=25 µm)
Figure 8B:
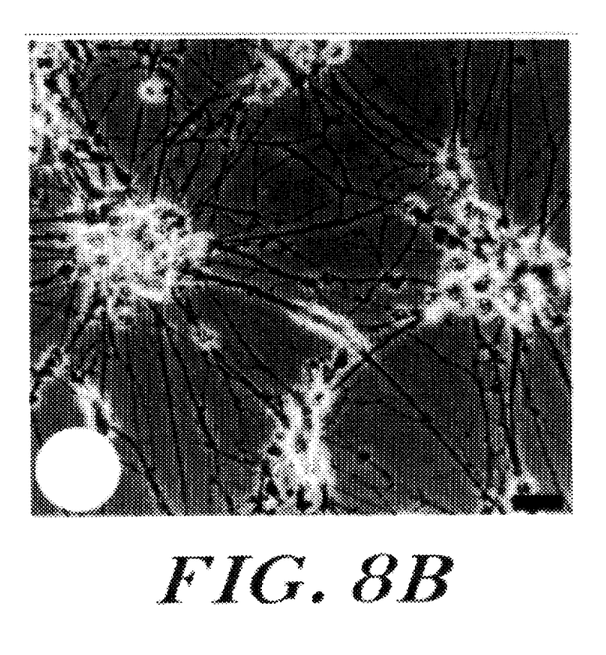
FIG. 8B is a phase contrast micrograph of SY5Y/TrkA cells treated for 8 days with 100 ng/ml NGF and then with normal growth for 6 days (bar=25 µm)

To assess reversibility of differentiation and dependence on NGF for survival, SY5Y/ET and SY5Y/TrkA cells were treated for 6 to 12 days with NGF and then were returned to normal growth medium. The slight NGF-induced neurite extension of SY5Y/ET cells reversed following removal of NGF (FIG. 8A). However, removal of NGF from differentiated SY5Y/TrkA cells did not reverse neurite extension or cause cell death (FIG. 8B), indicating that differentiation resulted from an endogenously directed event.

To determine whether differentiated SY5Y/TrkA cells produce NGF, culture supernatant of differentiated SY5Y/TrkA cells was added to PC12 cells which are highly NGF-responsive (Greene et al. (1976) *Proc. Natl. Acad. Sci. USA* 73:2424–2428). The PC12 cells did not extend neurites and, hence, there was no apparent NGF activity in the culture supernatant. Furthermore, treatment of differentiated SY5Y/TrkA cells with 100 or 300 nM of K252a or K252b, inhibitors of TrkA kinase, eliminated all detectable phosphotyrosine residues on TrkA and did not reverse differentiation. Hence, NGF- and aphidicolin-treated SHSY5Y cells and NGF-treated SY5Y/TrkA cells differ in that the differentiated SHSY5Y cells required NGF for survival (LoPresti et al. (1992) *Cell Growth Differentiation.* 3:627–635), whereas the differentiated SY5Y/TrkA cells did not require NGF or even the basal level of activity of the TrkA kinase.

To determine whether aphidicolin induces any unique effects independent of TrkA upregulation, SY5Y/TrkA cells were treated with NGF and aphidicolin as described in the experiments with SHSY5Y cells. There was no apparent difference in the differentiated SY5Y/TrkA cells induced by NGF and aphidicolin versus induction of NGF alone.

In contrast to SHSY5Y cells, SY5Y/TrkA cells treated with NGF and aphidicolin did not become dependent on NGF for survival. These results are summarized in TABLE 1, below. For neurite extension, only cells with neurites greater than or equal to 5 cell diameters were scored as positive. A very small percentage of SHSY5Y cells treated with NGF extend such long neurites; however, about 90% of these extend short neurites 1–2 cell diameters in length.

TABLE 1

| Cell Line → | SHSY5Y | SHSY5Y | SY5Y/ET | SYSY/TrkA | SY5Y/TrkA |
|---|---|---|---|---|---|
| Treatment → | NGF | NGF and aphidicolin | NGF | NGF | NGF and aphidicolin |
| Characteristics | | | | | |
| Neurite extension | + | +++ | + | +++ | +++ |
| Inhibition of cell proliferation | − | +++ | − | ++ | +++ |
| Dependence on NGF for survival | − | +++ | − | − | − |
| Irreversibility of differentiation | − | +++ | − | +++ | +++ |

−, 0–10% of cells;
+, 10–30%;
++, 30–60%;
+++, 70–100%.

Figure 9:
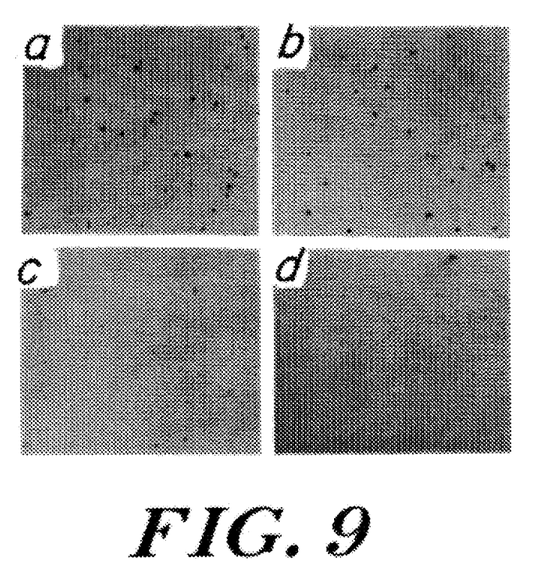
FIG. 9 is a photograph of soft agarose demonstrating the growth of SY5Y/ET (positions a and b) and SY5Y/TrkA (positions c and d) in the absence (positions a and c) or presence (positions b and d) of NGF, and scored after 21 days of culture.
Figure 10:
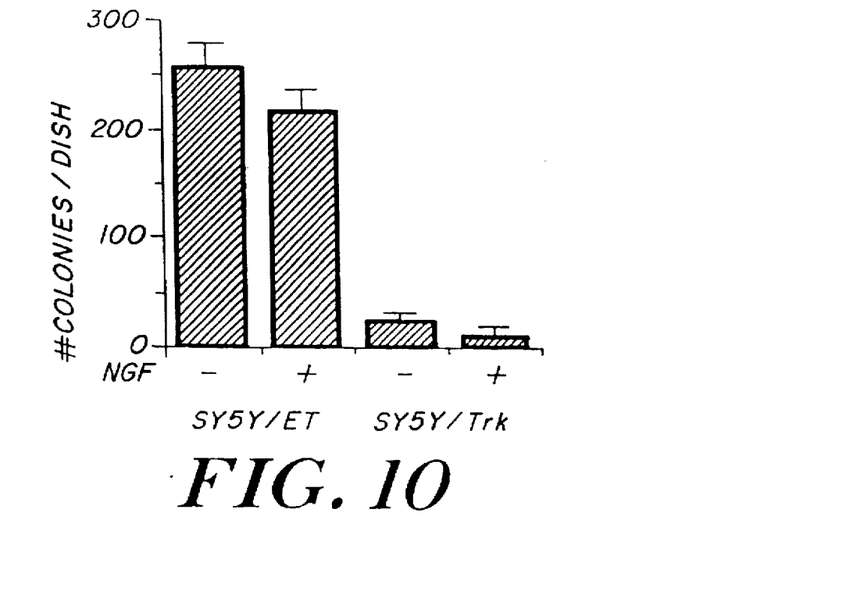
FIG. 10 is a graphic representation of the growth of SY5Y/ET or SY5Y/TrkA cells in soft agarose in the absence (−) or presence (+) of 100 ng/ml NGF.
Figure 11:
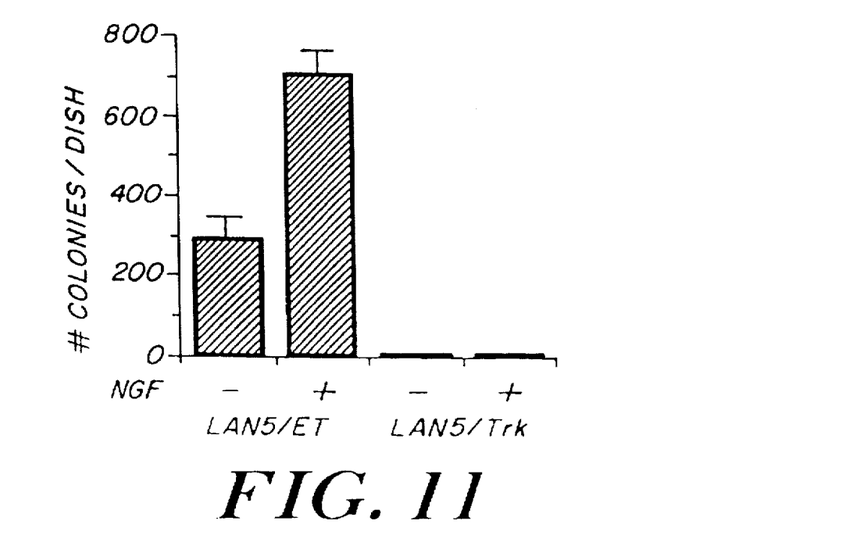
FIG. 11 is a graphic representation of the growth of LAN5/ET (designated as "empty" in figure) and LAN-5/ TrkA (designated as "trk" in figure) in soft agarose in the absence (−) or presence (+) of NGF.
Figure 12:
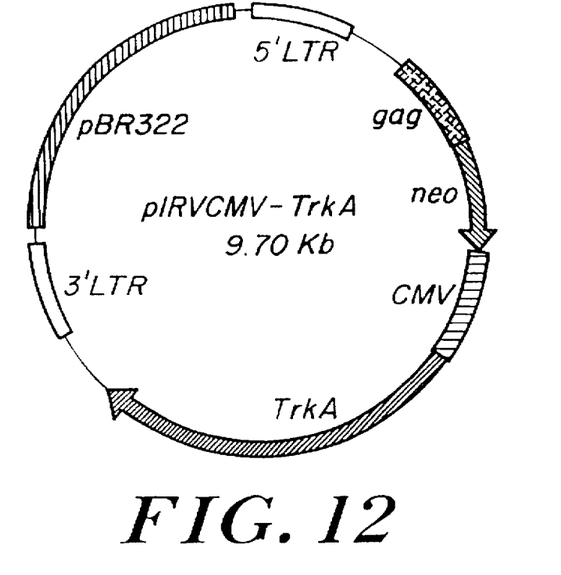
FIG. 12 is a map of the pIRVCMV-TrkA vector.
Figure 13:
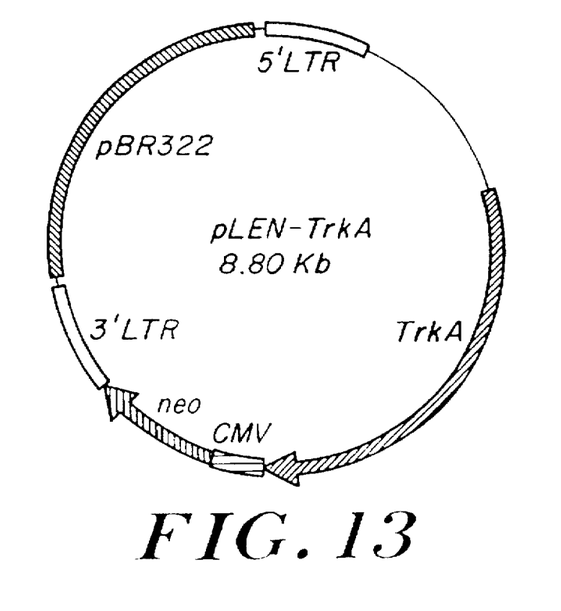
FIG. 13 is a map of the pLEN-TrkA vector.
Figure 14:
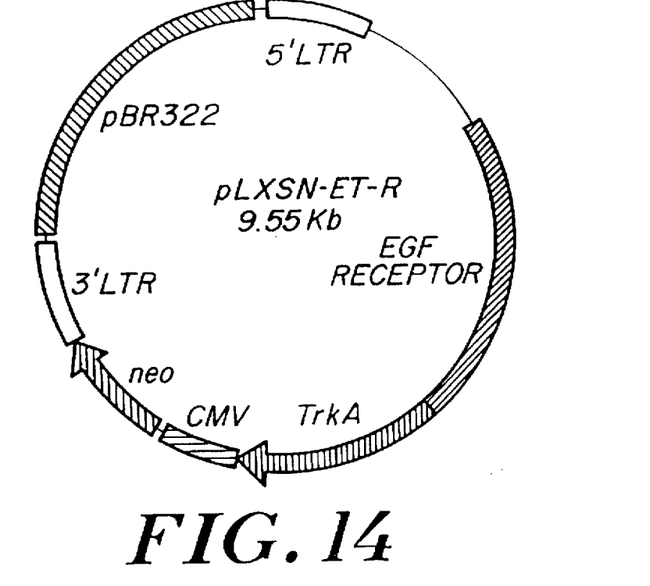
FIG. 14 is a map of the pLXSN vector which encodes a chimeric receptor including parts of both EGF-R and TrkA.

The effect of TrkA expression on anchorage-independent growth on soft agarose of SHSY5Y cells was assessed to measure tumorigenicity. SY5Y/ET cells had a much greater capacity to grow in soft agarose than SY5Y/TrkA; the colonies for SY5Y/ET were both more numerous and larger than those for SY5Y/TrkA (FIG. 9, positions a, b, c, and d). In addition, colonies which did not take up vital dye were more common for SY5Y/TrkA cells than for SY5Y/ET cells. Inclusion of NGF in the soft agarose had no apparent effect on either SY5Y/ET or SY5Y/TrkA (FIG. 9, positions b and d, and FIG. 10). These results indicate that cells containing the gene encoding the differentiation factor receptor were less tumorigenic than cells which did not contain the gene, and that similar results were obtained in another neuroblastoma cell line, LAN5, electroporated with trkA. FIG. 11 shows that these cells have a reduced ability to form colonies in soft agarose both in the presence and absence of added NGF.

The following examples illustrate the preferred modes of making and practicing the present invention, but are not meant to limit the scope of the invention since alternative methods may be utilized to obtain similar results.

EXAMPLES

1. Cell Culture

The neuroblastoma cell line SHSY5Y was derived as described (Biedler et al. (1978) *Cancer Res.* 38:3751–3747). Cells were grown at 37° C. in RPMI 1640 medium (GIBCO BRL, Gaithersburg, Md.) supplemented with 10% fetal bovine serum (Sigma Chemicals, St. Louis, Mo.) and 100 μμg/ml of gentamicin. For differentiation studies, cells were plated (1.5×10⁵ to 5×10⁵ cells/dish) in 35-mm Primaria dishes (Falcon, Franklin Lakes, NJ). One hundred ng/ml NGF (2.5 S; Bioproducts for Science, Indianapolis, IN) and/or 0.3 µM aphidicolin (Sigma Chemicals, St. Louis, Mo.) were added every 2–3 days. Cells proliferation was assessed by BrdU labelling, as described by LoPresti et al. (*Cell Growth Diff.* (1992) 3:627–635).

LAN5 cells are a human neuroblastoma derived as described by West et al. (CancerRes. (1977) 37:1372–1376). This cell line differs from the SH5Y5Y line in that the N-myc protooncogene is amplified in LAN5 cells but not in SH5Y5Y. Hence, the etiology leading to the SH5Y5Y tumor differs from the LAN5 tumor. Cells were grown at 37° C. in RPMI 1640 medium (GIBCO BRL, Gaithersburg, Md.) supplemented with 10% fetal bovine serum and 100 µg/ml gentamicin.

2. RNA Extraction and Northern Blotting

Total RNA was isolated by the single-step method of Chomczynski et al. (*Anal. Biochem.* (1987) 162:156–159). Poly A⁺RNA was selected with the PolyA Tract kit (Promega, Madison, Wis.), resolved by electrophoresis on a 1.0% agarose-formaldehyde gel, transferred to a Duralose membrane (Strategene, La Jolla, Calif.), and fixed with UV irradiation. The membranes were hybridized with [³²P] dCTP-random primer-labelled cDNA probes for c-myc and c-max (Blackwood et al. (1991) *Science* 251:1211–1217), the low affinity NGF receptor (Johnson et al. (1986) *Cell* 47:545–554), trkA (Martin-Zanca et al. (1989) *Mol. Cell. Biol.* 9:24–33), and trkB (Middlemas et al. (1991) *Mol. Cell. Biol.* 11:143–153). All blots were rehybridized with a cDNA probe for β-actin (Gunning et al. (1983) *Mol. Cell. Biol.* 3:787–795).

3. Preparation of Vectors

The pIRVCMV-TrkA vector was prepared using the pIRVCMV plasmid.

This plasmid includes an ampicillin resistance gene and origin of replication for growth in bacteria, a neomycin-resistance gene (neo) for selection in eukaryotic cells, a cytomegalovirus (CMV) promoter for expression of inserted genes, and long terminal repeats (LTR) for insertion into eucaryotic genomes (see FIG. 11). pIRVCMV was cleaved with BamHI and ClaI, and a CDNA including all of the coding sequence for TrkA was inserted downstream from the CMV promoter and ligated. The ligation mix was used to transform bacteria. A clone (pIRVCMV-TrkA) was selected and used for all further experiments (Hempstead et al. (1992). *Neuron* 9:883–896). Prior to electroporation, pIRVCMV-TrkA was cleaved with NotI. This procedure is designed to increase production of the TrkA protein. During insertion of pIRVCMV-TrkA into the genome, the plasmid is linearized. By cleaving at the NotI site, the linearization occurs in a region not required for expression of the trka sequence.

The plasmid pLEN-TrkA was prepared by cleaving the plasmid pLEN with EcoRI and then inserting the trka cDNA downstream of the promoter in the 5' LTR which includes a promoter to drive the expression of the trka gene. The ligation mixture was used to transform bacteria, and a clone (pLEN-TrkA/ was selected and used for all further experiments. Prior to electroporation pLEN-TrkA was cleaved with NdeI.

The plasmid pLXSN-ET-R which encodes a chimeric receptor was prepared by fusing sequences from the EGF-R and TrkA cDNA's (Obermeir et al. (1993) *EMBO J.* 12:933–941). Most of the EGF-R extracellular sequence was derived from a 1680 base pair (bp) XbaI-ApaI restriction fragment. An additional 418 bp at the 3' end of the larger fragment was derived by PCR. These fragments were ligated and cloned into a Bluescript vector (Stratogene, LaJolla, Calif.). Most of the TrkA intracellular domain was derived from a 1100 bp NarI-EcoRI restriction fragment. The remaining 364 bp were generated by PCR, ligated to the longer fragment via the NarI site and simultaneously cloned into a SmaI/EcoRI-linearized pT7T3 18U vector (Pharmacia, Piscataway, N.J.). These cDNA's were recovered by digestion of the plasmids with XbaI and PvuI, and from the pT7T3 vector by digestion with ScaI and EcoRI. These DNA's were ligated and cloned into a Bluescript plasmid. The insert was then excised and ligated into the PLXSN plasmid, thereby, creating the PLXSN-ET-R plasmid.

4. Electroporation and Selection of Cell Lines

5×10⁶ SHSY5Y cells were washed once with PBS and harvested using Hank's buffered saline solution (*Meth. Enzmol.* (1979) (Colowick and Kaplan, eds.) 58:119–131) supplemented with 1 mM of EDTA. Cells were electroporated in RPMI 1640 with 60 µg NotI linearized pIRVCMV or pIRVCMV-TrkA plasmids (Hempstead et al. (1992) *Neuron* 9:883–896) using a Bio-Rad Gene Pulser (Hercules, Calif.) (450 V, 960 µF, 0.4 cm gap). Cells were seeded onto 25-cm² tissue Primaria culture flasks (Falcon, Franklin Lakes, N.J.). Selection was performed for 2 weeks using the antibiotic G418 (400 µg/ml in RPMI 1640 and 10% FBS) (Gibco, Gaithersburg, Md. and Sigma Chemicals, St. Louis, Mo.) Multiple clones (>20) of G418-resistant cells were obtained and pooled to create cell lines SY5Y/ET (control vector) and SY5Y/TrkA (expression vector). These lines were maintained at 400 µg/ml in medium containing G418.

LAN5 cells were alternatively electroporated with the pLEN-TrkA or the pLXSN plasmid and selected as described above for SHSY5Y cells.

4. Anchorage-Independent Assay

Soft agarose cultures consisted of two layers. The lower layer was prepared by mixing equal volumes of 1.4% (W/V) agarose (SeaPlaque, FMC Bioproducts, Rockland, Me.) and 2×RPMI containing 20% FBS at 37° C. The lower layer was allowed to solidify and upper layer was poured within one hour. The upper layer consisted of equal volume of lower layer mix and cell suspension. Triplicate cultures were set up using 3,000 cells per 60 mm diameter petri dish. Cultures were fed every 5 days with 1 ml of upper layer. After 5 to 6 weeks, cultures were stained with 1 mg/ml of p-iodonitrotetrazolium violet (Sigma, St. Louis, Mo.). Colonies consisting of 20 or more cells were counted after 24 hours. (Small et al. (1987) *Mol. Cell. Biol.* 7:1638–1645).

5. Immunoprecipitation

Neuroblastoma cells were grown to near confluence in 75 cm² flasks and then incubated with 10 ml of methionine-minus RPMI 1640 containing 10% dialyzed fetal bovine serum and 0.04 mCi/ml ³²S-Protein Labelling Mix (Dupont, Wilmington, Del.). After 11 hours, crude membranes were prepared from 1.5×10⁷ cells and extracted with detergent as described by Ross et al. *Arch. Biochem. Biophys.* (1985) 242:540–548). Immunoprecipitations were performed for 1 hour at 4° C. using 2 µl 203 anti-TrkA C-terminus rabbit serum (Hempstead et al. (1992) *Neuron* 9:883–896) or normal rabbit serum. Immunoprecipitated proteins were analyzed by electrophoresis on an 8% SDS polyacrylamide gel. Protein bands were detected by fluorography using the Autoradiography Enhancer Entensify (Dupont, Wilmington, Del.).

6. Detection of Phosphorylation of TrkA

To detect phosphorylation of TrkA on tyrosine residues, 2×10⁷ neuroblastoma cells were extracted as described by Kaplan et al. *Cell* (1990) 61:125–133) and immunoprecipitated with 203 anti-TrkA serum (Hempstead et al., *ibid.*). These samples were applied to an 8% SDS polyacrylamide gel and transferred to Immobilon-P (Millipore, Bedford, Mass.). Phosphotyrosine-bearing protein was detected by Western blotting with RC20 anti-phosphotyrosine antibody-horseradish peroxidase conjugate (Transduction Laboratories, Lexington, Ky.) and a chemiluminescence reagent (Renaissance; Dupont, Wilmington, Del.).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of determining whether a differentiation factor receptor is capable of inhibiting the tumorigenicity of a neuroblastoma cell in the absence of a ligand for the receptor, the method consisting essentially of:

(a) transferring into neuroblastoma cells a vector comprising a nucleotide sequence which encodes a cell-surface receptor for a differentiation factor;

(b) culturing the cells under conditions suitable for the expression of said receptor, said culturing conducted in the absence of a ligand for said receptor; and (c) monitoring the culture for a reduction in cell proliferation and colony formation relative to a control culture.

2. A method according to claim 1, wherein the vector is transferred into the neuroblastoma cells by means of electroporation, transfection, transformation, or particle bombardment.

3. A method according to claim 1, wherein the culturing is performed in a semisolid medium.

4. A method according to claim 3, wherein the semisolid medium is soft agar or methylcellulose.

5. A method of reducing the ability of a neuroblastoma cell to proliferate, the method consisting essentially of:

(a) transferring into a neuroblastoma cell a vector comprising a nucleotide sequence which encodes a receptor selected from the group consisting of TrkA, TrkB, and a chimeric receptor comprising the intracellular domain of TrkA or TrkB and the extracellular domain of a different receptor; and (b) culturing the cell under conditions suitable for the expression of said receptor, said culturing conducted in the absence of a ligand for said receptor.

6. A method according to claim 5, wherein the vector encodes TrkA.

7. A method according to claim 5, wherein the vector encodes a chimeric receptor having the extracellular domain of the EGF receptor.

8. A method according to claim 5, wherein the vector encodes a chimeric receptor having the extracellular domain of the PDGF receptor.

9. A method according to claim 5, wherein the vector is transferred into the neuroblastoma cell by means of electroporation, transfection, transformation, or particle bombardment.

10. A method according to claim 5, wherein the culturing is performed in a semisolid medium.

11. A method according to claim 10, wherein the semisolid medium is soft agar or methylcellulose.

\* \* \* \* \*